Figure 1:
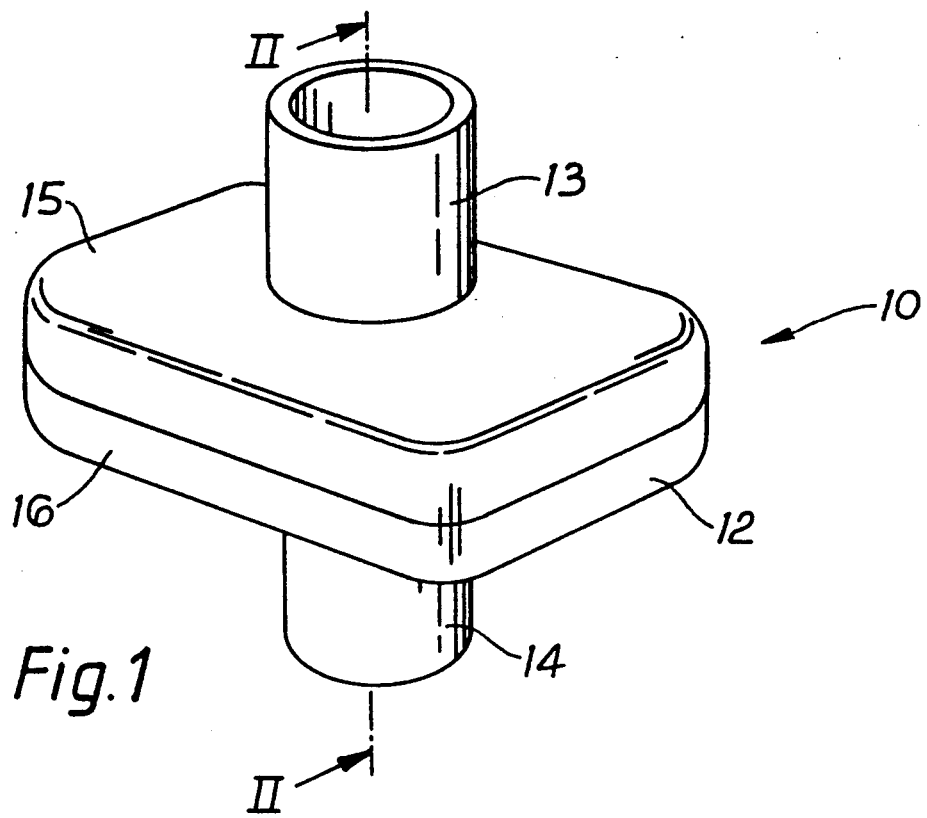

United States Patent [19]

Hicks

[11] Patent Number: 5,195,527
[45] Date of Patent: Mar. 23, 1993

[54] RESPIRATORY FILTERS

[75] Inventor: Richard B. Hicks, Kingston-upon-Thames, United Kingdom

[73] Assignee: Intersurgical Limited, Twickenham, United Kingdom

[21] Appl. No.: 776,348

[22] PCT Filed: May 21, 1990

[86] PCT No.: PCT/GB90/00795
§ 371 Date: Nov. 18, 1991
§ 102(e) Date: Nov. 18, 1991

[87] PCT Pub. No.: WO90/14122
PCT Pub. Date: Nov. 29, 1990

[30] Foreign Application Priority Data

May 19, 1989 [GB] United Kingdom ............... 8911627

[51] Int. Cl.$^5$ ........................................... A61M 16/10
[52] U.S. Cl. ........................... 128/205.12; 128/205.27; 128/204.17
[58] Field of Search ..................... 128/204.13, 204.17, 128/205.12, 205.27, 205.29; 55/502, 503

[56] References Cited

U.S. PATENT DOCUMENTS

| | | |
|---|---|---|
| 2,284,964 | 6/1942 | Mautz et al. ................ 128/205.12 |
| 3,782,083 | 1/1974 | Rosenberg . |
| 3,932,153 | 1/1976 | Byrns .......................... 128/205.29 X |
| 4,090,513 | 5/1978 | Tagawa ....................... 128/204.13 X |
| 4,113,627 | 9/1978 | Leason . |
| 4,159,954 | 7/1979 | Gangemi . |
| 4,200,094 | 4/1980 | Gedeon et al. ................ 128/201.13 |
| 4,704,143 | 11/1987 | Percy ............................... 55/502 X |
| 4,771,770 | 9/1988 | Artemenko et al. .......... 128/201.13 |
| 5,035,236 | 7/1991 | Kanegaonkar ............. 128/205.27 X |
| 5,062,874 | 11/1991 | Lagare et al. ................... 55/502 X |

FOREIGN PATENT DOCUMENTS

| | | |
|---|---|---|
| 0256534 | 2/1988 | European Pat. Off. . |
| 0265163 | 4/1988 | European Pat. Off. . |
| 0269589 | 6/1988 | European Pat. Off. . |
| 1440661 | 6/1976 | United Kingdom . |
| 1575752 | 9/1980 | United Kingdom . |
| 1598172 | 9/1981 | United Kingdom . |
| 2231509 | 11/1990 | United Kingdom ........... 128/205.29 |

Primary Examiner—V. Millin
Assistant Examiner—Raleigh W. Chiu
Attorney, Agent, or Firm—Young & Thompson

[57] ABSTRACT

A respiratory filter included in a respiratory system used in anaesthesia and/or patient ventilation, comprises a two-part housing 15 and 16 having coaxial ports 13 and 14 for connection to breathing tubes. Optionally a heat/moisture exchanger 25 spans the housing in addition to a planar filter member 24 which is held between parts 15 and 16 so as to be perpendicular to the direction of gas flow through the housing. According to the invention deflectors 30 and 19 are located relative to the ports 13 and 14 so as to spread incoming gases over the opposed surfaces of members 24 and 25 in order to utilize their total surface areas, thereby reducing the overall size of the filter and reducing "apparatus dead space". Each deflector has a through bore so as to utilize also the central area of the filter. Curved fins 26 and 27 radiate from each port 13 and 14. In an alternative embodiment of the invention the housing has two ports at one end, each having an associated deflector, and the fins 25 or 27 are omitted on the housing part having the two ports.

11 Claims, 4 Drawing Sheets

RESPIRATORY FILTERS

This invention relates to an improved respiratory filter included in a respiratory system of the kind used in anaesthesia and/or patient ventilation. Such filters may be used both for bacteriological control and as heat and moisture exchangers.

Such a filter comprises a housing containing a filter medium, with said housing representing an enlargement of the breathing tube in which it is included, and with ports at opposite ends of the housing being fitted to lengths of the tube, usually a flexible, plastics pipe of corrugated construction, passing respectively to and away from the patient. The filter medium spans the housing between the ports so that air and/or other gases inhaled and exhaled by the patient must pass through it. The filter medium employed in one type of such filter in common use comprises a generally rectangular block of corrugated paper. In another such filter in common use the filter medium is a permeable disc held in the housing to be perpendicular to the direction of flow of gases between the ports. The latter type has the advantage of being relatively less bulky than the former, but what both types have in common is that the housing is generally funnel-shaped at its ends where it tapers toward each port from the opposed surface of the filter medium. The empty space thus provided at each end of the filter housing is undesirable not only because it increases the size and bulk of the filter but more significantly because it represents "apparatus dead space" (see e.g. British Standards Institute's, BS 6015:1980) in which exhaled gases can collect so as to be reinspired. Nevertheless substantial "dead space" has been provided because the further the relatively wide surface of the filter member is from each port the more opportunity gases will have to spread from the port before impinging on the filter member. Secondly, if the filter member were too close to each port it would be difficult to breath through the filter and in the case of weak patients e.g. in an intensive care unit it is essential that breathing should be obstructed as little as possible by the filter.

A principal object of the present invention is to provide a filter, included in a breathing system, in which "apparatus dead space" within the filter housing is substantially reduced without the prejudicial consequences to be expected from so doing.

Another problem inherent in the use of such filters is that because only a relatively small, central area of the filter medium is directly opposed to the housing port through which gases flow toward it the gases pass predominately through a central portion of the filter medium and its peripheral portion relatively unused. The solution most commonly employed has been to distance the filter member further from each port to give the gases more room to diverge from the ports, but this makes the filter larger and more bulky and increases "apparatus dead space". Concentration of use of the filter medium to a central area reduces its effectiveness, or at least its effective life.

Another object of the present invention is to provide a smaller, less bulky filter with reduced "apparatus dead space" yet in which the filter medium will be more uniformly employed.

In British Patent Specification No. 1 440 661 there is proposed a filter for either liquid or gaseous media in which the filter member is enclosed between cover plates continguous therewith each having ribs which define with the filter member a plurality of inlet and outlet passages. A filter of this kind would not be suitable as a respiratory filter because of the resistance it would offer to gases passing through it. This Specification proposes "substantially conical jet spreaders" arranged to deflect the incoming or outgoing medium from the inlet port or to the outlet port.

The arrangement of substantially conical deflectors adjacent the inlet and outlet ports of a respiratory filter would assist in the reduction of "apparatus dead space" but at the expense of unacceptably increasing resistance to flow. Moreover solid deflectors would produce a "shadow" on the central area of the filter member aligned therewith, preventing full and substantially uniform uitilisation of the surface area of the filter member.

Another object of the present invention is to provide a filter improved in that the deflector aligned with each port does not create a "shadow effect" on the region of the filter member with which it is aligned.

In accordance with the present invention there is provided a filter included in a respiratory system for use in anaesthesia and/or patient ventilation, the filter comprising a housing having at least one port for connection to a line for the supply of a gaseous medium to and from a patient, the port being of smaller cross section than the housing, means in the housing for maintaining at least one filter member therein to span the interior of the housing transversely to the direction of flow of said medium when passing from said port into the housing and a deflector member positioned relative to the junction between the port and housing so as to disperse said medium entering the housing from said port over the opposed, planar surface of said filter member, characterised in that the deflector member has a through bore generally aligned with said port and an outer surface which increases in cross section away from said port.

The filter may additionally be a heat- and/or moisture-exchanger.

Preferably the deflector member is spaced from said port and said bore of the deflector member is coaxially aligned with said port.

The deflector means preferably presents a curved outer surface toward said port and is preferably trumpet-horn-shaped.

The housing may have a second port coaxial with the first-mentioned port and at the opposite end of the housing, and there may be positioned in the housing spaced from the second port a second deflector member which reduces in cross section toward said second port and which has a through bore aligned with said second port.

There are preferably disposed in the interior of the housing to radiate from the or each said port a series of curved fins circumferentially spaced about said port further to deflect the gaseous medium deflected by the or each said deflector member.

In an alternative embodiment the housing may additionally have second and third ports at the opposite end of the housing to the first-mentioned port, and there may be positioned in the housing spaced from each said second and third port a respective deflector member which reduces in cross section toward the associated port and which has a through bore aligned with said associated port.

The housing is preferably of two part construction and said means for maintaining the filter member within the housing preferably comprises an inner wall of each part arranged so that when the two parts of the housing are joined the filter member may be gripped between the opposed, inner walls of the housing parts.

A hygroscopic member may additionally be located within and spans the housing parallel with the filter member. Preferably the hygroscopic member is located on the side of the filter member remote from the port to be connected to the patient.

Figure 5:
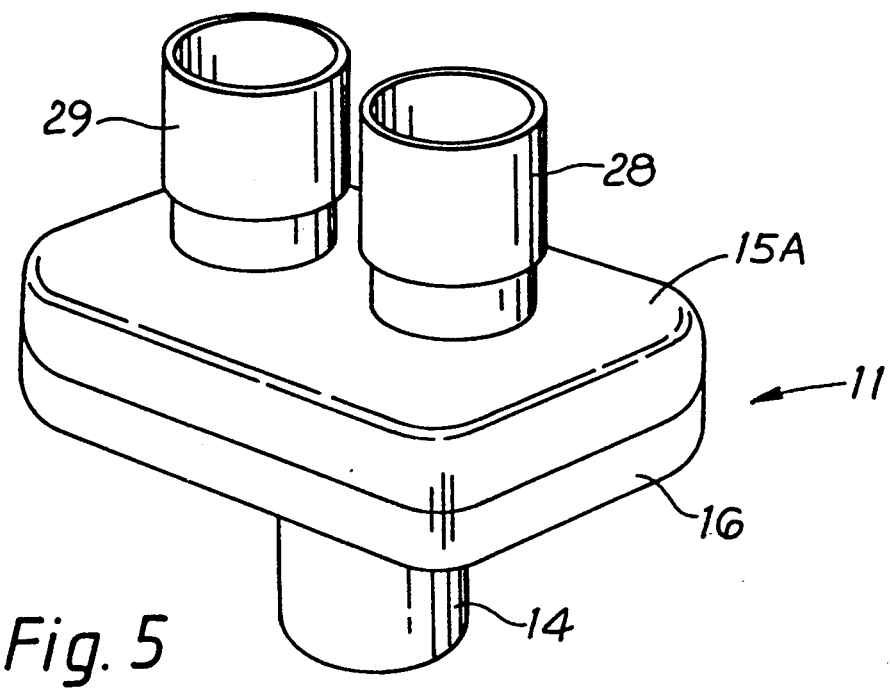
Figure 2:
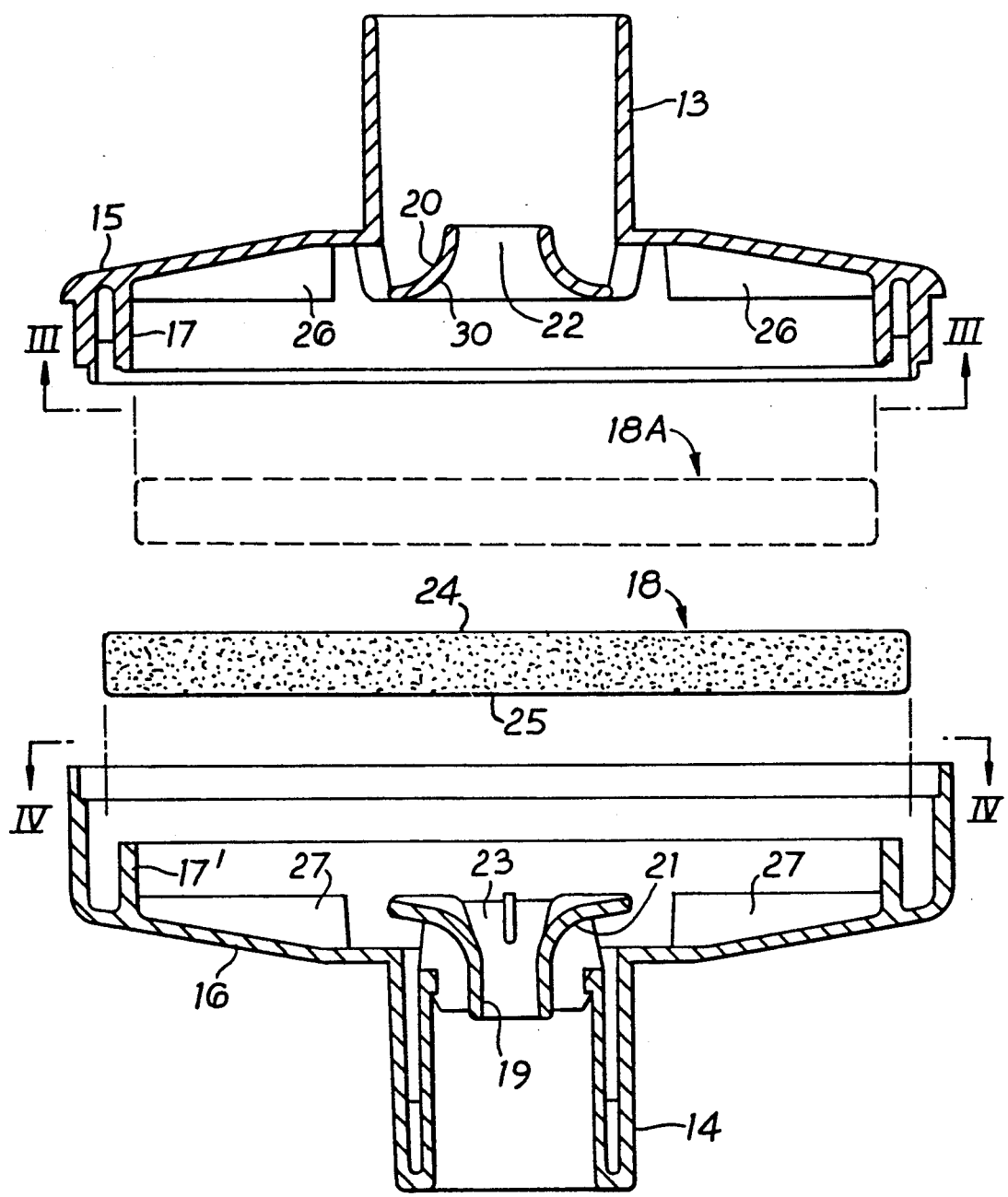
Figure 3:
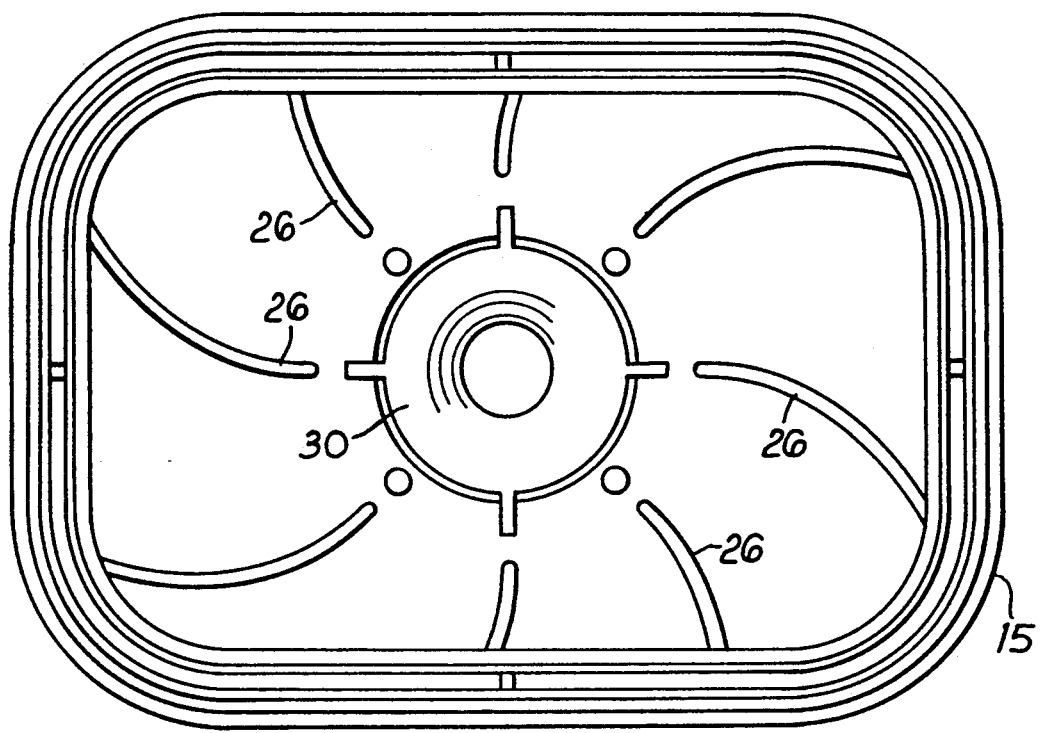
Figure 4:
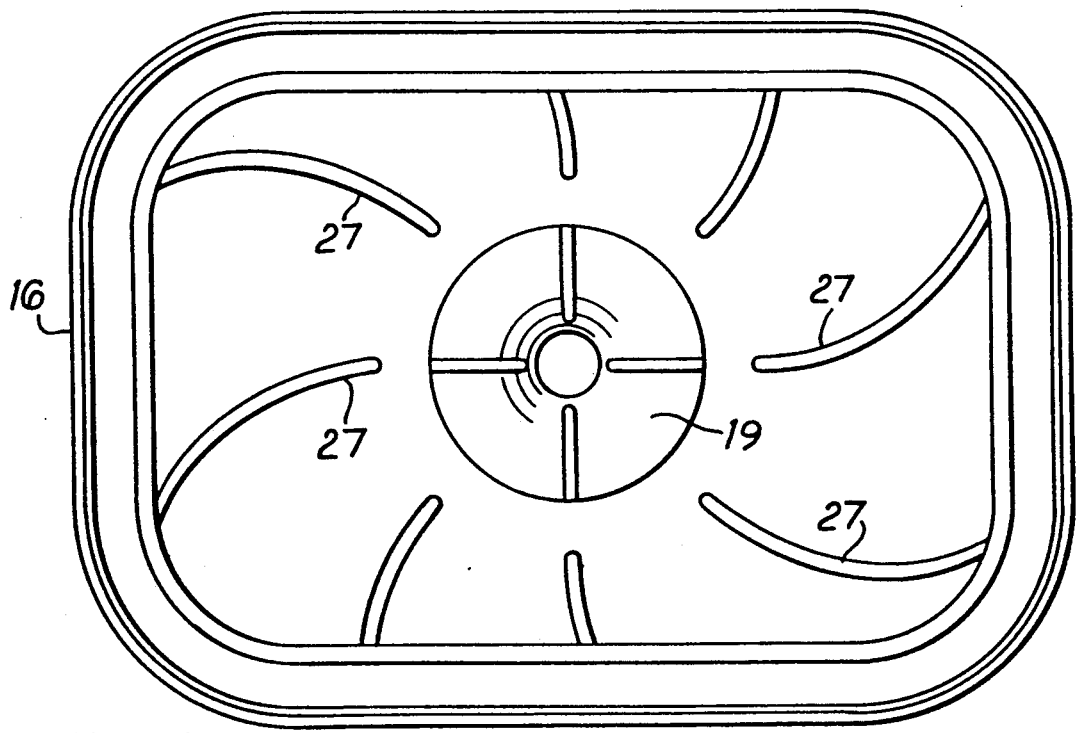
Figure 6:
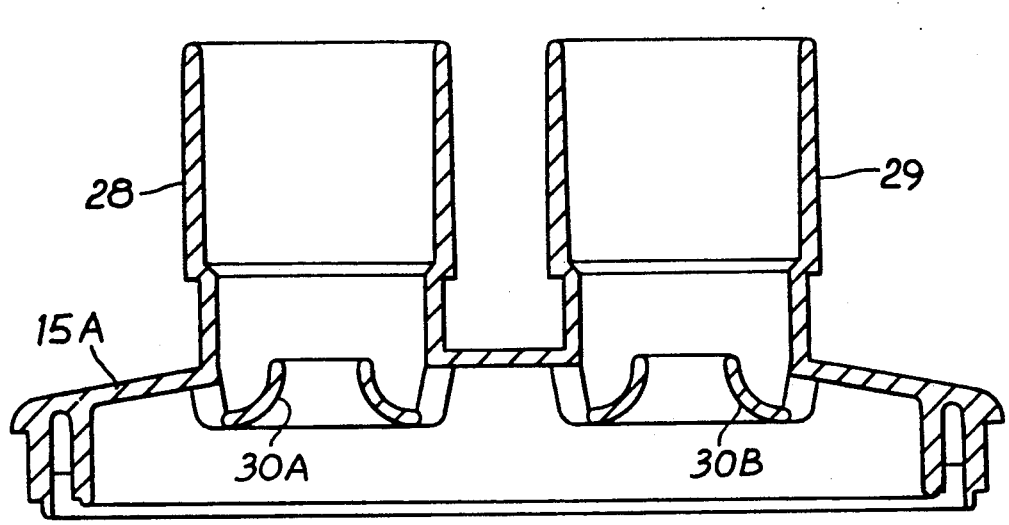
Figure 7:
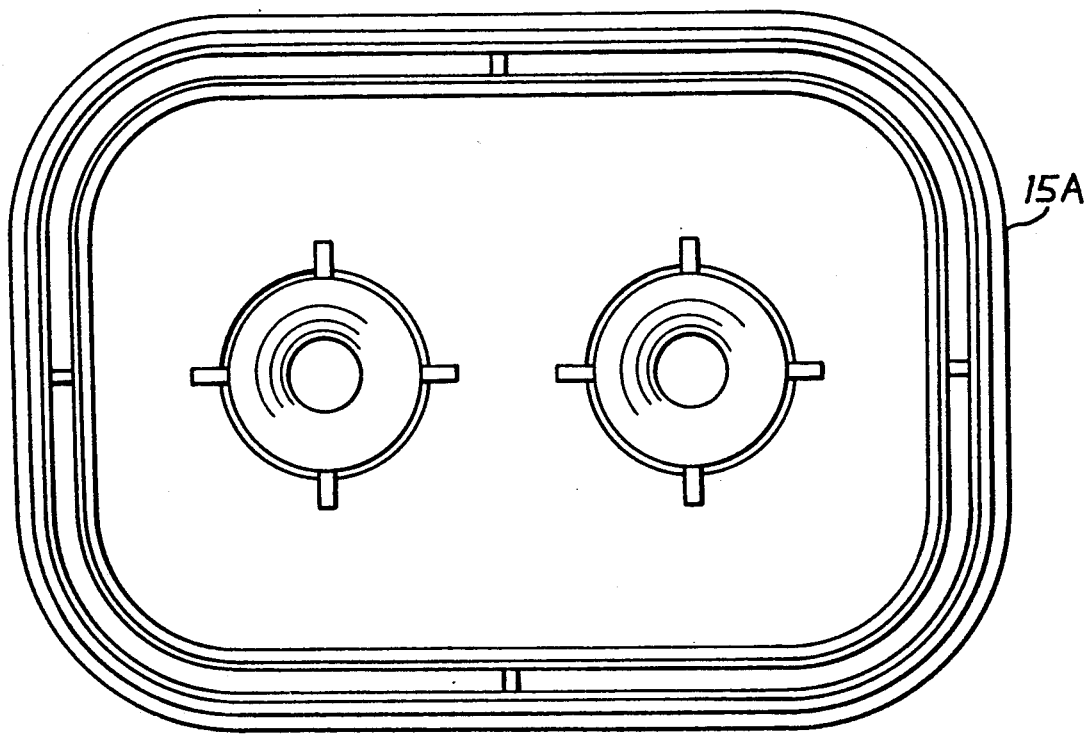

Preferred embodiments of the present invention will now be described with reference to the accompanying drawings, in which:

FIG. 1 is a perspective view of a first filter in accordance with the invention, FIG. 2 is an exploded sectional elevation of the filter of FIG. 1, taken on the line II—II of FIG. 1, FIG. 3 is an underplan view of the top part of the filter of FIGS. 1 and 2 taken on the line III—III of FIG. 2, FIG. 4 is a plan view of the bottom part of the filter of FIGS. 1 and 2 taken on the line IV—IV of FIG. 2, FIG. 5 is a view similar to that of FIG. 1 of a second filter in accordance with the invention, and FIGS. 6 and 7 are respectively a sectional elevation and an underplan view of the top part (only) of the filter of FIG. 5.

The filter 10 illustrated in FIGS. 1 to 4 is intended for inclusion in a breathing system (not shown) for anaesthesia or patient ventilation. As is conventional, the filter housing 12 has ports 13 and 14 at opposite ends to which flexible plastic tubes (not shown) may be connected, one passing to the patient and the other to atmosphere and/or to apparatus for dispensing or controlling a gaseous mixture to be administered to the patient.

The filter housing 12 is made in two parts 15 and 16. Each part is double-walled, having a relatively lower inner peripheral wall 17, 17'. When the two parts 15 and 16 are brought together a flat filter member 18 is located and held between the inner walls 17, 17'. The bacteriological filter member 18 is typically a disc of electrostatically charged polymer fibers. The outer walls of the parts 15 and 16 are then welded together ultrasonically. This arrangement has a number of advantages. The outer surface of the finished filter housing 12 is smooth, having no flange which might cause discomfort to the patient. By this method of entrapping the filter member 18 there is considerable tolerance of its dimensional variations. Thus the planar filter member 18 spans the interior of the housing 12 perpendicularly to the direction of flow of gases between the ports 13 and 14.

Co-axial with each port 13 and 14 and spaced slightly from its orifice within the housing is a respective deflector member 30 and 19. Each deflector member 30 and 19 is trumpet-shaped, tapering toward the associated port, so as to present to gases flowing into the housing from the port a curved periphery 20 and 21. Being hollow, each deflector member 30 and 19 has a central bore 22 and 23 which widens inwardly of the housing. The disposition and configuration of the deflector members 30 and 19 is such that gases flowing into the housing 12 from the associated port 13 and 14 are divided, deflected and spread over the opposed surfaces 24 and 25 of the filter member 18. However central regions of the filter surfaces are not in "shadow" from the deflectors. The central bores of the deflectors ensure that some, but not the whole of the inflowing gases are directed to the central regions of the filter surfaces 24 and 25.

The deflector member 19 also deflects the expired heat and moisture from a patient's breath entering via port 14 such that an optional hygroscopic element 18A will retain the heat and moisture. A portion of this heat and moisture will be returned to the patient on an inspiratory breath. Preferably and as shown the hyrgoscopic element 18A, which is a matrix of polyester fibres in which hygroscopic polymer fibres are embedded, is located on the side of the filter element 18 remote from the port 14 connected to the patient. Alternatively the element 18A may be located on the side of the filter 18 nearer the patient.

Deflection of the gases is further enhanced by the provision of a series of curved fins 26 and 27 circumferentially spaced around and radiating from the orifice of each port 13 and 14 (FIGS. 3 and 4).

The modified filter of FIGS. 5, 6 and 7 is for use in breathing systems which include separate, valve-controlled paths for gases inhaled and exhaled by the patient. Hitherto this has been achieved by fitting a Y-junction to one of the ports of a two-port filter housing. In accordance with this embodiment of the present invention no Y-junction is necessary. A single port 14 at one end of the housing is, as before, connected by a single tube to a patient airway but separate tubes (not shown) are connected to individual ports 28 and 29 at the other end of the housing.

The filter 11 is also a two-part construction, the bottom part 16 being identical to the bottom part utilised in the embodiment of FIGS. 1-4. Therefore only the different, top part 15A of the filter 11 is illustrated in FIGS. 6 and 7. Each of the paired ports 28 and 29 has located adjacent its orifice within the housing a respective deflector member 30A and 30B. Each deflector member 30A and 30B resembles the deflector 30 of the embodiment of FIGS. 1-4. Fins such as 26 and 27 are not provided on the part 15A.

I claim:

1. A respiratory filter included in a respiratory system for use in anaesthesia and/or patient ventilation, the respiratory filter (10) comprising a housing (12) containing at least one filter member (18), said housing (12) having at least one port (14) for connection to a line for the supply of a gaseous medium to and from a patient, the port (14) being of smaller cross section than the housing (12), means (17, 17') in the housing (12) for maintaining said at least one filter member (18) therein to span the interior of the housing (12) transversely to the direction of flow of said medium from said port (14) into the housing (12) and a deflector member (19) positioned relative to the junction between the port (14) and housing (12) so as to disperse said medium entering the housing (12) from said port (14) over the opposed, planar surface (25) of said filter member (18), wherein the deflector member (19) has a through bore (23) generally aligned with said port (14) and an outer surface (21) which increases in cross section away from said port (14).

2. A filter as claimed in claim 1, wherein said filter member is a heat- and/or moisture-exchange element.

3. A filter as claimed in claim 1, wherein the deflector member (19) is spaced from said port (14) and said bore (23) of the deflector member (19) is coaxially aligned with said port (14).

4. A filter as claimed in claim 1, wherein the deflector member (19) presents a curved outer surface (21) toward said port (14).

5. A filter as claimed in claim 1, wherein the deflector member (19) is trumpet-horn-shaped.

6. A filter as claimed in claim 1, wherein the housing (12) has a second port (13) coaxial with the first-mentioned port (14) and at the opposite end of the housing, (12) and in that there is positioned in the housing (12) spaced from the second port (13) a second deflector member (30) which reduces in cross section toward said second port (13) and which has a through bore (22) aligned with said second port (13).

7. A filter as claimed in claim 1, wherein there are disposed in the interior of the housing (12) to radiate from said at least one port (14, 13) a series of curved fins (27, 26) circumferentially spaced about said at least one port (14, 13) further to deflect the gaseous medium deflected by said at least one deflector member (19, 30).

8. A filter as claimed in claim 1, wherein the housing (12) additionally has second and third ports (28,29) at the opposite end of the housing (12) to the first-mentioned port (14), and in that there is positioned in the housing (12) spaced from each said second and third port (28,29) a respective deflector member (30A,30B) which reduces in cross section toward the associated port (28,29) and which has a through bore aligned with said associated port (28, 29).

9. A filter as claimed in claim 1, wherein the housing (12) is of two part construction and in that said means for maintaining the filter member (18) within the housing comprises an inner wall (17,17') of each part (15,16) arranged so that when the two parts (15,16) of the housing (12) are joined the filter member (18) is gripped between the opposed, inner walls (17,17') of the housing parts (15,16).

10. A filter as claimed in claim 1, wherein a hygroscopic member (18A) is additionally located within and spans the housing (12) parallel with the filter member (18).

11. A filter as claimed in claim 10, wherein the hygroscopic member (18A) is located on the side of the filter member (18) remote from the port (14) to be connected to the patient.

* * * * *